United States Patent [19]

Maughan

[11] Patent Number: 4,465,629

[45] Date of Patent: Aug. 14, 1984

[54] METHOD TO INCREASE COLOR FASTNESS OF STABILIZED ALOE VERA

[76] Inventor: Rex G. Maughan, P.O. Box 29041, Phoenix, Ariz. 85038

[21] Appl. No.: 476,419

[22] Filed: Mar. 17, 1983

[51] Int. Cl.$^3$ .................. C07G 17/00; A61K 35/78
[52] U.S. Cl. .................. 260/236.5; 424/195
[58] Field of Search .................. 424/195; 260/236.5

[56] References Cited

U.S. PATENT DOCUMENTS 3,878,197  4/1975  Maret .................. 260/236.5
3,892,853  7/1975  Cobble .................. 424/195
4,178,372  12/1979  Coats .................. 424/195

Primary Examiner—Jerome D. Goldberg
Assistant Examiner—John W. Rollins, Jr.
Attorney, Agent, or Firm—Richards, Harris & Medlock

[57] ABSTRACT

A process for imparting color fastness to stabilized aloe vera gel. The process including the steps of admixing with a heated aloe vera gel the antioxidant effective to prevent oxidation of said gel, adjustment of the gel to a pH in the range of from about 3.0 to about 3.5 and cooling the admixed gel to 23° C. or lower in less than about 15 minutes.

10 Claims, No Drawings

METHOD TO INCREASE COLOR FASTNESS OF STABILIZED ALOE VERA

TECHNICAL FIELD

The present invention relates to the color fastness of stabilized aloe vera which surprisingly increases the color fastness of the stabilized aloe vera gel over a prolonged period of time. In particular, the process requires the addition of an effective amount of an antioxidant be added to the gel during the final heating stage of the stabilization process, adjustment of the pH from about 3 to about 3.5 followed by the rapid cooling of the aloe vera gel to about 23° C. or below within about 15 minutes.

BACKGROUND ART

Aloe vera is a tropical or subtropical plant which is the last few years has been accepted and increasingly demanded for its medicinal qualities. Aloe vera gel has long been used in the treatment of rashes, minor cuts, treatment of jelly fish stings, animal stings and the like. American Indians utilized aloe vera by breaking a leaf from an aloe vera plant and squeezing the gel from the leaf onto the area desired to be treated. Use of aloe vera did not extend beyond the growing environment of the plant because the raw gel could not be stored. The therapeutic qualities of the gel diminished rapidly upon exposure to air and light. The use and demand of aloe vera gel has expanded as a result of several stabilization processes. These processes preserved the therapeutic qualities of the gel for up to about 12 months. However the gel compositions even though stabilized and therapeutically effective undergo color changes. Although color changes have little relation to the therapeutic effectiveness of stabilized gel, they are rarely acceptable psychologically to the user. In some products, the color change is totally unacceptable. Recently, aloe vera has become widely used in cosmetic products where discoloration of the gel is unacceptable. The process of the present invention achieves color stabilization with a surprisingly simple process which achieves about a 100% increase in the color fastness of stabilized aloe vera. The process of the present invention increases the color fastness of the product by about 24 months.

SUMMARY OF THE INVENTION

In one aspect, the present invention is directed to a process for improving the color fastness of stabilized aloe vera gel. The process requires the processing of aloe vera to stabilize it from decomposition during the final heating step of which an effective amount of antioxidant, such as sodium bisulfide is added. The pH is adjusted to a range of from about 3.0 to about 3.5 and the stabilized aloe vera gel is then rapidly cooled to about 23° C. or below within about 15 minutes. The preferred embodiment calls for a process wherein the aloe vera gel is stabilized by heating the gel in the range of from about 30° C. to about 70° C. for a sufficient period of time to kill bacteria present in the gel, adding sodium bisulfide and adjusting the pH of the aloe vera in the range of 3.3 to 3.5 and rapidly cooling with the gel to about 23° C. or below within about 10 minutes.

DETAILED DESCRIPTION

Aloe vera gel or juice color fastness may be improved by the method of the present invention for a prolonged period up to about 24 months. Aloe vera leaves are harvested and processed immediately to prevent degradation of the aloe vera gel matrix. Leaves are cut, washed and soaked in a bacteriacide and fungicide. After soaking in bacteriacide or fungicide, the leaves are rinsed with sterile water and the leaves processed to mechanically separate the gel matrix from the outer cortex. The gel matrix is then filtered to remove plant debris from the gel matrix. The gel matrix is then heated in the range of 30° C. to 70° C. and preferably from 45° C. to 70° C. for a period of time sufficient to kill bacteria in the gel. The experience has shown that heating the gel from about 45 minutes to about 90 minutes is sufficient to kill the bacteria. During the stabilization process, various additives may be incorporated into the stabilized gel as discussed and explained in my copending application Ser. No. 386,702 filed June 9, 1982 entitled "Controlled Temperature Process for Manufacturing of Improved Stabilized Aloe Vera", which is hereby incorporated by reference. During the final few minutes of the heating cycle, an antioxidant is added in an amount effective to prevent oxidation of the stabilized gel. The antioxidant may be selected from the group consisting of sodium sulfite, sodium bisulfite, sodium metabisulfite, calcium edetate, propyl gallate and glycine or combinations thereof. It has been found that from about 0.01% to about 0.1% by weight of antioxidant is sufficient. In the preferred embodiment, sodium bisulfite is incorporated into the stabilized gel product in the range from about 0.01% to about 0.1% by weight.

The pH of the stabilized gel is adjusted to the range of 3.0 to 3.5. The pH may be adjusted with a suitable acid such as tartaric acid, sodium tartarate, fumaric acid, maleic acid, phosphoric acid, acetic acid, or a combination of these. Preferably, the pH is adjusted in the range of from about 3.3 to 3.5.

In the preferred embodiment, a metallic ion scavenger is added to neutralize metallic ions which may be present in the gel. It is believed that metallic ions present in the stabilized gel act as a catalyst and contribute to color changes. The metal ion most prevalent in aloe vera is copper. Suitable metal scavengers include tetra sodium EDTA (ethylene-diamine tetraacedic acid). Up to about 0.2% and preferably, from about 0.001% to about 0.2% by weight of tetra sodium EDTA is used. It has also been found beneficial to add calcium phosphate to the gel because it interacts with reactive ion groups on the organic molecules of the aloe vera gel. Incorporation of up to about 1.0% and preferably from about 0.1% to about 1.0% by weight of calcium phosphate has been found to be effective. A bleaching agent may also be added to the stabilized gel such as sodium bicarbonate. In the preferred embodiment, from about 0.05% to about 0.5% by weight of sodium bicarbonate is admixed with the gel.

Admixture of these ingredients into the stabilized gel can be aided by the utilization of a surfactant. Tween 80, a polyoxyethylene (20) sorbitan monooleate, sold by ICI Chemicals has been found to be a suitable surfactant.

Once admixed, the aloe vera is rapidly cooled to ambient temperature (about 23° C.) or below and preferably about 20° C. The temperature of the aloe vera must be reduced within about 15 minutes and preferably within 10 minutes. The combined process of adding an antioxidant, adjusting the pH to the aforementioned range and the rapid cooling of the stabilized aloe vera produces a surprising increase in color fastness over a long period of time.

While the invention has been described in relation to its preferred embodiments, it is to be understood that various modifications thereof will now be apparent to one skilled in the art upon reading the specification and it is intended to cover all such modifications as fall within the scope of the appended claims.

I claim:

1. A process for imparting color fastness to a stabilized aloe vera gel comprising:
   (a) heating clear gel which has been separated from the leaf of an aloe vera plant to a temperature in the range of from about 30° C. to about 70° C. for a sufficient period of time to kill bacteria;
   (b) adding to said gel an antioxidant in an amount effective to prevent oxidation of said gel;
   (c) cooling said aloe vera gel to about 23° C. or lower in less than 15 minutes; and
   (d) adjusting the pH of said gel to the range of 3.0 to 3.5.

2. The process of claim 1 wherein said antioxidant is selected from the group consisting of sodium sulfite, sodium bisulfite, sodium metabisulfite, calcium edetate, propyl gallate, and glycine, and combinations thereof.

3. The process of claim 2 wherein said antioxidant is present in an amount of from 0.01% to 0.1% by weight of said gel.

4. The process of claim 3 wherein said antioxidant is sodium bisulfite.

5. the process of claim 4 further comprising the step of admixing into said gel prior to cooling the following components: from 0% to about 0.5% by weight of sodium bicarbonate; from 0% to about 1.0% by weight of calcium phosphate, and from 0% to about 0.2% by weight of terta sodium ethylenediamine tetraacedic acid.

6. A process for imparting color fastness to a stabilized aloe vera gel comprising:
   (a) heating clear gel which has been separated from the leaf of an aloe vera plant to a temperature in the range of from about 45° C. to about 70° C. for a sufficient period of time to kill bacteria;
   (b) adding to said gel an antioxidant in an amount effective to prevent oxidation of said gel;
   (c) cooling said aloe vera gel to about 23° C. or lower in less than 10 minutes; and
   (d) adjusting the pH of said gel to the range of 3.3 to 3.5.

7. The process of claim 6 wherein said antioxidant is selected from the group consisting of sodium sulfite, sodium bisulfite, sodium metabisulfite, calcium edetate, propyl gallate, glycine, and combinations thereof.

8. The process of claim 7 wherein said antioxidant is present in an amount of from 0.01% to 0.1% by weight of said gel.

9. The process of claim 8 wherein said antioxidant is sodium bisulfite.

10. The process of claim 9 further comprising the step of admixing into said gel prior to cooling the following components: from 0.05% to 0.5% by weight of sodium bicarbonate; from 0.1% to 1.0% by weight of calcium phosphate, and from 0.001% to 0.2% by weight of tetra sodium ethylenediamine tetraacedic acid.

* * * * *

UNITED STATES PATENT AND TRADEMARK OFFICE
CERTIFICATE OF CORRECTION

PATENT NO. : 4,465,629
DATED : August 14, 1984
INVENTOR(S) : Rex G. Maughan

It is certified that error appears in the above-identified patent and that said Letters Patent is hereby corrected as shown below:

Column 1, line 18, change "is" to --in--.

Signed and Sealed this

Seventeenth Day of September 1985

[SEAL]

Attest:

DONALD J. QUIGG

Attesting Officer

*Commissioner of Patents and Trademarks—Designate*